United States Patent
Gilbert et al.

(10) Patent No.: US 9,084,722 B2
(45) Date of Patent: Jul. 21, 2015

(54) BIOLOGIC SCAFFOLD FOR PREVENTION OF PULMONARY FIBROSIS

(75) Inventors: Thomas Gilbert, Pittsburgh, PA (US); Michelle Manni, Pittsburgh, PA (US); Tim D. Oury, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 569 days.

(21) Appl. No.: 13/132,708

(22) PCT Filed: Dec. 4, 2009

(86) PCT No.: PCT/US2009/066754
§ 371 (c)(1),
(2), (4) Date: Jul. 6, 2011

(87) PCT Pub. No.: WO2010/065843
PCT Pub. Date: Jun. 10, 2010

(65) Prior Publication Data
US 2011/0262498 A1  Oct. 27, 2011

Related U.S. Application Data

(60) Provisional application No. 61/200,949, filed on Dec. 5, 2008.

(51) Int. Cl.
*A61K 9/00* (2006.01)
*A61K 35/22* (2015.01)

(52) U.S. Cl.
CPC ............... *A61K 9/0075* (2013.01); *A61K 9/008* (2013.01); *A61K 9/0078* (2013.01); *A61K 35/22* (2013.01)

(58) Field of Classification Search
None
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,554,389 A | 9/1996 | Badylak et al. | |
| 5,573,784 A | 11/1996 | Badylak et al. | |
| 5,645,860 A | 7/1997 | Knapp, Jr. et al. | |
| 5,753,267 A | 5/1998 | Badylak et al. | |
| 5,762,966 A | 6/1998 | Knapp, Jr. et al. | |
| 5,771,969 A | 6/1998 | Garay | |
| 5,866,414 A | 2/1999 | Badylak et al. | |
| 6,099,567 A | 8/2000 | Badylak et al. | |
| 6,485,723 B1 | 11/2002 | Badylak et al. | |
| 6,576,265 B1 | 6/2003 | Spievack | |
| 6,579,538 B1 | 6/2003 | Spievack | |
| 6,696,270 B2 | 2/2004 | Badylak et al. | |
| 6,766,801 B1 | 7/2004 | Wright | |
| 6,783,776 B2 | 8/2004 | Spievack | |
| 6,793,939 B2 | 9/2004 | Badylak | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 2003/0044444 A1 | 3/2003 | Malaviya et al. | |
| 2005/0013870 A1 | 1/2005 | Freyman et al. | |
| 2006/0134079 A1 | 6/2006 | Sih et al. | |
| 2007/0166396 A1* | 7/2007 | Badylak et al. | ............... 424/551 |
| 2008/0086072 A1* | 4/2008 | Bonutti et al. | .................. 604/21 |

OTHER PUBLICATIONS

Santamauro et al., CHEST, vol. 105, No. 1, Jan. 1994, pp. 310-312.*
Badylak, Stephen F., "The extracellular matrix as a biologic scaffold material", Biomaterials, 2007, pp. 3587-3593, vol. 28.
Badylak, Stephen F. et al., "Immune Response to Biologic Scaffold Materials", Semin Immunol., 2008, pp. 109-116, vol. 20(2).
Badylak, Stephen F. et al., "Extracellular matrix as a biological scaffold material: Structure and function", Acta Biomaterialia, 2009, pp. 1-13, vol. 5.
Beattie, Allison J. et al., "Chemoattraction of Progenitor Cells by Remodeling Extracellular Matrix Scaffolds", Tissue Engineering: Part A, 2009, pp. 1119-1125, vol. 15, No. 5.
Brennan, Ellen P. et al., "Chemoattractant activity of degradation products of fetal and adult skin extracellular matrix for keratinocyte progenitor cells", J Tissue Eng Regen Med., 2008, pp. 491-498, vol. 2(8).
Brennan, Ellen P. et al., "Antibacterial Activity within Degradation Products of Biological Scaffolds Composed of Extracellular Matrix", Tissue Eng., 2006, pp. 2949-2955, vol. 12(10).
Brown, Bryan et al., "The Basement Membrane Component of Biologic Scaffolds Derived from Extracellular Matrix", Tissue Engineering, 2006, pp. 519-526, vol. 12, No. 3.
Downey, Douglas M. et al., "Functional Comparison of Staple Line Reinforcements in Lung Resection", Ann Thorac Surg, 2006, pp. 1880-1883, vol. 82.
Downey, Douglas M. et al., "Functional Assessment of a New Staple Line Reinforcement in Lung Resection", Journal of Surgical Research, 2006, pp. 49-52, vol. 131.
Englert, Judson M. et al. "A Role for the Receptor for Advanced Glycation End Products in Idiopathic Pulmonary Fibrosis", The American Journal of Pathology, 2008, pp. 583-591, vol. 172, No. 3.
Fattman, Cheryl L. et al., "Increased sensitivity to asbestos-induced lung injury in mice lacking extracellular superoxide dismutase", Free Radic Biol Med., 2006, pp. 601-607, vol. 40(4).

(Continued)

*Primary Examiner* — Allison Fox
*Assistant Examiner* — Yvonne Pyla
(74) *Attorney, Agent, or Firm* — The Webb Law Firm

(57) ABSTRACT

Provided herein are methods of preventing, lessening or treating pulmonary fibrosis in a subject. The methods comprise delivering an amount of a powdered extracellular matrix (ECM)-derived material to the respiratory system of the subject effective to prevent, lessen or treat pulmonary fibrosis in a subject. Also provided is an apparatus for delivering the powdered ECM-derived material to a subject.

17 Claims, 8 Drawing Sheets

(56) References Cited

OTHER PUBLICATIONS

Fattman, Cheryl L. et al., "Altered Expression of Extracellular Superoxide Dismutase in Mouse Lung after Bleomycin Treatment", Free Radical Biology & Medicine, 2001, pp. 1198-1207, vol. 31, No. 10.

Gao, Fai et al., "Extracellular Superoxide Dismutase Inhibits Inflammation by Preventing Oxidative Fragmentation of Hyaluronan", J Biol Chem., 2008, pp. 6058-6066, vol. 283(10).

Gilbert, Thomas W. et al., "Degradation and Remodeling of Small Intestinal Submucosa in Canine Achilles Tendon Repair", The Journal of Bone & Joint Surgery, 2007, pp. 621-630, vol. 89-A, No. 3.

Gilbert, Thomas W. et al., "Morphologic Assessment of Extracellular Matrix Scaffolds for Patch Tracheoplasty in a Canine Model", Ann Thorac Surg, 2008, pp. 967-974, vol. 86.

Gilbert, Thomas W. et al., "Production and characterization of ECM powder: implications for tissue engineering applications", Biomaterials, 2005, pp. 1431-1435, vol. 26.

Gilbert, Thomas W. et al., "Repair of the Thoracic Wall With an Extracellular Matrix Scaffold in a Canine Model", Journal of Surgical Research 2008, pp. 61-67, vol. 147.

Kliment, Corrine R. et al., "Extracellular Superoxide Dismutase Protects Against Matrix Degradation of Heparan Sulfate in the Lung", Antioxid Redox Signal., 2008, pp. 261-268, vol. 10(2).

Kliment, Corrine R. et al., "Oxidative Stress Alters Syndecan-1 Distribution in Lungs with Pulmonary Fibrosis", The Journal of Biological Chemistry, 2009, pp. 3537-3545, vol. 284, No. 6.

Li, F. et al., "Low-Molecular-Weight Peptides Derived from Extracellular Matrix as Chemoattractants for Primary Endothelial Cells", Endothelium, 2004, pp. 199-206, vol. 11.

Liang, Chun-Chi et al., "In vitro scratch assay: a convenient and inexpensive method for analysis of cell migration in vitro", Nature Protocols, 2007, pp. 329-333, vol. 2, No. 2.

Meltzer, Eric B. et al., "Idiopathic pulmonary fibrosis", Orphanet Journal of Rare Diseases, 2008, pp. 1-15, vol. 3:8.

Moeller, Antje et al., "The bleomycin animal model: a useful tool to investigate treatment options for idiopathic pulmonary fibrosis?", Int J Biochem Cell Biol., 2008, pp. 362-382, vol. 40(3).

O'Connor, Robert E. et al., "Powders", 2005, pp. 702-719, The Science and Practice of Pharmacy, 21.sup.st. Edition, Lippincott Williams & Wilkins.

Record, Rae D. et al., "In vivo degradation of C-labeled small intestinal submucosa (SIS) when used for urinary bladder repair", Biomaterials, 2001, pp. 2653-2659, vol. 22.

Reing, Janet E. et al., "Degradation Products of Extracellular Matrix Affect Cell Migration and Proliferation", Tissue Engineering: Part A, 2009, pp. 605-614, vol. 15, No. 3.

Sciarra, John J. et al., "Aerosols", 2005, pp. 702-719, The Science and Practice of Pharmacy, 21.sup.st. Edition, Lippincott Williams & Wilkins.

Vracko, Rudolf, "Basal Lamina Scaffold-Anatomy and Significance for Maintenance of Orderly Tissue Structure", Review Article, 1974, pp. 314-338.

\* cited by examiner

BIOLOGIC SCAFFOLD FOR PREVENTION OF PULMONARY FIBROSIS

STATEMENT REGARDING FEDERALLY-SPONSORED RESEARCH AND DEVELOPMENT

This invention was made with government support under Grant No. R01 HL63700, awarded by the National Institutes of Health. The government has certain rights in this invention.

Provided herein are compositions and related methods useful in promoting normal remodeling and preventing fibrosis in the lung.

Fibrosis is the formation or development of excess fibrous connective tissue in an organ or tissue as a reparative or reactive process, as opposed to a formation of fibrous tissue as a normal constituent of an organ or tissue. Pulmonary fibrosis is a fibrosis (fibrotic condition) involving the lung. Pulmonary fibrosis may arise from damage to the lung tissue, as is present in interstitial lung disease (ILD, also known as diffuse parenchymal lung disease). ILD may be classified according to the cause, for example and without limitation: inhaled substances, including silicosis, asbestosis, berylliosis and hypersensitivity pneumonitis; drug induced, such as from antibiotics, chemotherapeutic drugs (e.g., bleomycin) and antiarrhythmic agents; connective tissue disease, such as systemic sclerosis, dermatomyositis, systemic lupus erythematosus and rheumatoid arthritis; infection, such as atypical pneumonia, pneumocystis pneumonia (PCP) and tuberculosis; idiopathic, such as sarcoidosis, idiopathic pulmonary fibrosis and Hamman-Rich syndrome; or malignancy, such as lymphangitic carcinomatosis.

Idiopathic pulmonary fibrosis (IPF) is a debilitating disease characterized by inflammation, fibroblast proliferation, and excessive extracellular matrix deposition in the lung. The pathogenesis of pulmonary fibrosis has been studied widely in animal models. The most widely used model to study pulmonary fibrosis in rodents is the bleomycin model (Meltzer E B, et al. Idiopathic pulmonary fibrosis. *Orphanet J Rare Dis* 2008; 3:8 and Moeller A, et al. The bleomycin animal model: A useful tool to investigate treatment options for idiopathic pulmonary fibrosis? *Int J Biochem Cell Biol* 2008; 40(3):362-382). While the mechanisms for injury are still not fully understood, it appears that the pathology begins with epithelial damage followed by activation of alveolar macrophages and infiltration of the lung tissue by circulating inflammatory cells that release cytokines such as tumor necrosis factor (TNF)-$\alpha$ and interleukin (IL)-1$\beta$. Ultimately, this pro-inflammatory environment leads to the recruitment and proliferation of fibroblasts/myofibroblasts that produce transforming growth factor (TGF)-$\beta$ and deposit large quantities of collagenous, fibrotic tissue. Currently, pulmonary transplantation is the only viable option for patients with IPF (Meltzer E B, et al. Idiopathic pulmonary fibrosis. *Orphanet J Rare Dis* 2008; 3:8 and Moeller A, et al. The bleomycin animal model: A useful tool to investigate treatment options for idiopathic pulmonary fibrosis? *Int J Biochem Cell Biol* 2008; 40(3):362-382).

SUMMARY

Provided herein are compositions, drug products, apparatus and methods for prevention and/or treatment of pulmonary fibrosis. It has been found that delivery of ECM-derived materials, for example powdered or solubilized ECM-derived materials, to a subject's respiratory system lessens development of fibrosis and improves outcome in subjects exposed to conditions that result in pulmonary fibrosis, as is the case with, for example, ILD.

The ECM-derived material may be isolated and prepared from (derived from), for example and without limitation, urinary bladder tissue, trachea or lung tissue. In one non-limiting embodiment, the extracellular matrix-derived material comprises epithelial basement membrane and, optionally, subjacent tunica propria. In another, the extracellular matrix-derived material comprises tunica submucosa. In yet another, extracellular matrix-derived material comprises epithelial basement membrane, subjacent tunica propria and tunica submucosa. In certain non-limiting embodiments, the extracellular matrix-derived material is isolated from small intestinal submucosa or the dermis of the skin.

Methods of preventing or lessening development of pulmonary fibrosis in a subject also are provided. The methods comprise, without limitation, delivering to an airway of a subject an ECM-derived material to reduce, lessen or prevent (e.g., an amount effective to reduce, lessen or prevent) development of fibrosis in a subject exposed to a pulmonary fibrosis-causing agent or condition. The ECM-derived material may be powdered or solubilized. The ECM-derived material may be administered prior to or after exposure to a fibrosis-inducing event, such as exposure to a chemotherapeutic agent, radiotherapy, asbestos, etc. The pulmonary fibrosis-causing agent or condition (e.g., event) includes, without limitation, agents that cause ILD, including, without limitation, the following conditions: silicosis, asbestosis, berylliosis and hypersensitivity pneumonitis; drug induced, such as from antibiotics, chemotherapeutic drugs (e.g., bleomycin) and antiarrhythmic agents; radiation-induced fibrosis, often arising from radiotherapy, for example in cancer patients; exposure to a chemical agent, such as mustard gas; bronchiolitis obliterans; connective tissue disease, such as systemic sclerosis, dermatomyositis, systemic lupus erythematosus and rheumatoid arthritis; infection, such as atypical pneumonia, pneumocystis pneumonia (PCP) and tuberculosis; idiopathic, such as sarcoidosis, idiopathic pulmonary fibrosis and Hamman-Rich syndrome; or malignancy, such as lymphangitic carcinomatosis.

An apparatus is provided according to certain embodiments of the present invention. The apparatus comprises an airway delivery system comprising a composition comprising an ECM-derived material, such as a powdered and/or solubilized ECM-derived material. In certain embodiments, the airway delivery system is a metered dose inhaler, a device which is able to deliver to a patient one or more unit doses of a dry powder or aerosolized (e.g., nebulized or spray) liquid composition. The composition may be a dry powder or a liquid that can be aerosolized. The composition, e.g. in a metered dose inhaler, may comprise a propellant to assist in aerosolizing and propelling the drug product into a subject's respiratory system. The powdered ECM-derived material may have any effective size range, mean and distribution that can be effectively delivered to the respiratory system, and particularly the lungs of a subject to prevent or lessen development, or treat pulmonary fibrosis. In one example, the powdered ECM-derived material has a maximum particle size of 250 μM (meaning the ECM-derived material can pass through a screen having a mesh size of 250 μM); a maximum particle size of 75 μM; or a maximum particle size of 5 μM. In one non-limiting embodiment, the ECM-derived material comprises basement membrane and tunica propria obtained from porcine urinary bladder. In another embodiment, the ECM-derived material is digested, solubilized ECM.

DETAILED DESCRIPTION

Figure 1:
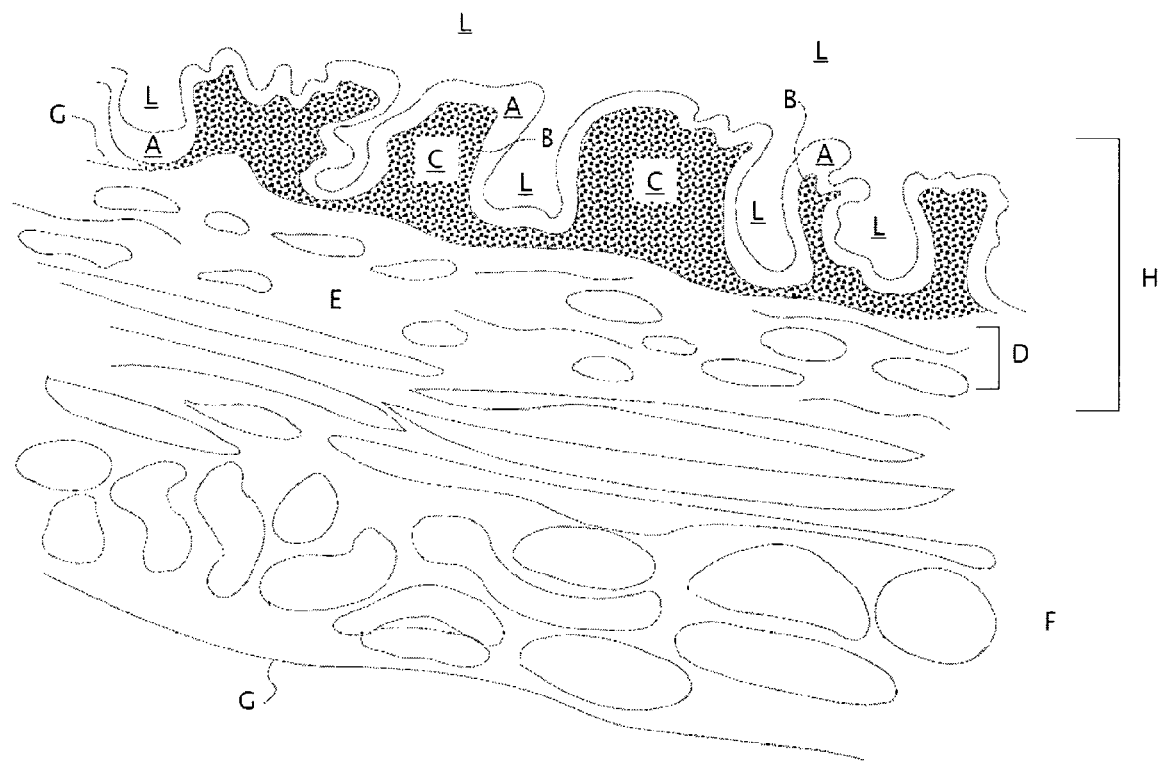
FIG. 1 is a schematic of a cross-sectional view of the wall of the urinary bladder (not drawn to scale). The following structures are shown: epithelial cell layer (A), basement membrane (B), tunica propria (C), muscularis mucosa (D), tunica submucosa (E), tunica muscularis externa (F), tunica serosa (G), tunica mucosa (H), and the lumen of the bladder (L).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

Described herein are methods for preventing, lessening or treating pulmonary fibrosis in a subject, as well as drug products useful in such methods. The methods include delivery of an extracellular matrix-derived (ECM-derived) material to the respiratory system, including the nasal cavity, trachea and lungs of a subject in an amount effective to prevent, lessen or treat pulmonary fibrosis in a subject.

Biologic scaffolds composed of mammalian extracellular matrix (ECM) have been shown to promote site-specific remodeling of musculoskeletal, cardiovascular, urogenital, and dermal tissues. The species and tissue origin of the ECM scaffolds vary, but the most commonly used and studied ECM scaffolds are derived from porcine small intestinal submucosa (SIS) and urinary bladder matrix (UBM). The mechanisms by which these ECM scaffolds promote tissue remodeling are also not fully understood, but appear to include the presentation of a three-dimensional microenvironment supportive of cell growth and migration that transmits biochemical and mechanical cues to the cells, and rapid degradation with subsequent release of small peptide fragments that possess innate bioactivity, specifically chemotaxis for progenitor cells and antibacterial behavior. This combination of microenvironmental cues and release of matricryptic peptides is responsible for the presence of an accommodative, tissue remodeling response as opposed to a cytotoxic, pro-inflammatory immune response. ECM scaffolds that are fully decellularized and not chemically crosslinked elicit a predominantly M2 type macrophage response.

ECM scaffolds have recently received attention for treatment of airway injury in several pre-clinical models. Recent studies have shown that ECM scaffold materials can prevent air leakage into the pleural cavity when used as a primary treatment or when used as reinforcement for a surgical staple line after partial lung resection (Downey D M, et al. Functional comparison of staple line reinforcements in lung resection. *Ann Thorac Surg* 2006; 82(5):1880-1883; Downey D M, et al. Functional assessment of a new staple line reinforcement in lung resection. *J Surg Res* 2006; 131(1):49-52; and Gilbert T W, et al. Repair of the thoracic wall with an extracellular matrix scaffold in a canine model. *J Surg Res* 2008; 147(1):61-67). SIS-ECM used for reinforcement of surgical staple lines showed significant improvement in intrabronchial pressures as compared to other reinforcement materials. Repair of the lung with a UBM-ECM scaffold showed moderately dense well-organized collagenous tissue formation at the site of resection without evidence of inflammation, necrosis, or scarring in the lung. In addition, UBM-ECM has recently been shown to promote the formation of a pseudostratified, columnar, ciliated epithelium when used for patch tracheoplasty in a canine model (Gilbert T W, et al. Morphologic assessment of extracellular matrix scaffolds for patch tracheoplasty in a canine model. *Ann Thorac Surg* 2008; 86(3):967-973; discussion 973-974).

ECM-derived material can be used for a large number of medical applications including, but not limited to, wound healing, tissue remodeling, and tissue regeneration. For example and without limitation, the scaffold can be used for wound healing. As used herein a composition manufactured from an ECM-derived material is useful in preventing and treating pulmonary fibrosis. The ECM-derived material is shown to ameliorate or lessen the occurrence of fibrosis in instances where pulmonary fibrosis can develop or progress. As an example, pulmonary fibrosis may develop as part of the progress of ILD, which, as indicated above, can have a variety of causes, including and without limitation: inhaled substances, including silicosis, asbestosis, berylliosis and hypersensitivity pneumonitis; drug induced, such as from antibiotics, chemotherapeutic drugs (e.g., bleomycin) and antiarrhythmic agents; connective tissue disease, such as systemic sclerosis, dermatomyositis, systemic lupus erythematosus and rheumatoid arthritis; infection, such as atypical pneumonia, pneumocystis pneumonia (PCP) and tuberculosis; idiopathic, such as sarcoidosis, idiopathic pulmonary fibrosis and Hamman-Rich syndrome; or malignancy, such as lymphangitic carcinomatosis.

A "drug product" is a compound, composition, formulation, apparatus, etc. comprising an "active agent", which is a compound or composition that has a specific pharmacological effect. A drug product is preferable "pharmaceutically acceptable," meaning that it is suitable for administration to a subject for a stated purpose, which is typically referred to as an "indication". Irrespective of whether a drug product or other composition, compound or material may or may not cause harm by its administration to a subject, it may be "pharmaceutically acceptable" if benefits of the composition, compound, material or drug product outweigh its risks. In one aspect, a compound, composition, material, excipient or drug product is pharmaceutically acceptable if it meets the requirements of an applicable regulatory agency, such as the US Food and Drug Administration, or any other applicable regulatory body, which includes compounds, compositions, materials or drug products that are Generally Recognized As Safe (GRAS). In a broader sense, a composition, compound, material or drug product and it is material is not biologically or otherwise undesirable for its intended use, that is, the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

As used throughout, by a "subject" is meant an animal or human. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human, including patients.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s).

The ECM-derived material is preferably biocompatible. By "biocompatible," it is meant that a polymer compositions and its normal in vivo degradation products are substantially non-toxic and non-carcinogenic in a patient within useful, practical and/or acceptable tolerances. In one non-limiting embodiment, the compositions, and/or devices are "biocompatible" to the extent they are acceptable for use in a human veterinary patient according to applicable regulatory standards in a given jurisdiction. In another example the biocompatible material, when administered to a patient, does not cause a substantial adverse reaction or substantial harm to cells and tissues in the body, for instance, the polymer composition or device does not cause necrosis or an infection resulting in harm to tissues.

As used herein, the terms "extracellular matrix" and "ECM" refer to a complex mixture of structural and functional biomolecules and/or biomacromolecules including, but not limited to, structural proteins, specialized proteins, proteoglycans, glycosaminoglycans, and growth factors that surround and support cells within mammalian tissues.

Generally, any type of extracellular matrix (ECM) can be used to prepare the ECM-derived material (for example and without limitation, see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). By "ECM-derived material" it is meant a composition that is prepared from a natural ECM or from an in vitro source wherein the ECM is produced by cultured cells and comprises one or more polymeric components (constituents) of native ECM.

According to one non-limiting example of the ECM-derived material, ECM is isolated from a vertebrate animal, for example, from a warm blooded mammalian vertebrate animal including, without limitation, human, monkey, pig, cow, sheep, etc. The ECM may be derived from any organ or tissue, including without limitation, urinary bladder, intestine, trachea, lung, liver, heart, esophagus, spleen, stomach and dermis. The ECM can comprise any portion or tissue obtained from an organ, including, for example and without limitation, submucosa, epithelial basement membrane, tunica propria, etc. In one non-limiting embodiment, the ECM is isolated from urinary bladder, which may or may not include the basement membrane. In another non-limiting embodiment, the ECM includes at least a portion of the basement membrane. The ECM material may or may not retain some of the cellular elements that comprised the original tissue such as capillary endothelial cells or fibrocytes.

In one non-limiting embodiment, the ECM is harvested from urinary bladders (also known as urinary bladder matrix or UBM), for example and without limitation, porcine urinary bladders. Briefly, the ECM can be prepared by removing the urinary bladder tissue from a pig and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria (layers B and C of FIG. 1).

In another embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

The ECM can be sterilized by any of a number of standard methods without loss of function. For example and without limitation, the material can be sterilized by propylene oxide or ethylene oxide treatment, gamma irradiation treatment (0.05 to 4 mRad), gas plasma sterilization, peracetic acid sterilization, or electron beam treatment. Treatment with glutaraldehyde results in sterilization as well as increased cross-linking of the ECM. This treatment substantially alters the material such that it is slowly resorbed or not resorbed at all and incites a different type of host remodeling, which more closely resembles scar tissue formation or encapsulation rather than constructive remodeling, which may not be desirable in the context of the present invention. If desired, cross-linking of the protein material within the ECM can also be induced with, for example and without limitation, carbodiimide isocyanate treatments, dehydrothermal methods, and photooxidation methods. In one non-limiting embodiment, the ECM is disinfected by immersion in 0.1% (v/v) peracetic acid, 4% (v/v) ethanol, and 96% (v/v) sterile water for two hours. The ECM material is then washed twice for 15 minutes with PBS (pH=7.4) and twice for 15 minutes with deionized water. The ECM-derived material may be further processed by optionally drying, desiccation, lyophilization, freeze drying, glassification, etc. The ECM-derived material optionally can be further digested, for example and without limitation by hydration (if dried), acidification, enzymatic digests with, for example and without limitation, trypsin or pepsin and neutralization, producing, for example, a solubilized ECM-derived material having increased solubility in a solvent, such as a water-based solvent.

Commercially available ECM preparations can also be used to manufacture the ECM-derived material described herein. In one non-limiting embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another non-limiting embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

Gilbert, T. W., et al. (Biomaterials, 2005. 26(12): p. 1431-5)) describe the preparation of one non-limiting embodiment of ECM-derived material. In that method, ECM is isolated from porcine urinary bladder. The bladder is harvested immediately following euthanasia of market weight pigs (approximately 120 kg). The ECM isolation is performed by removing the tunica muscularis externa and tunica submucosa layers, leaving the basement membrane and tunica propria intact. The UBM is then washed in a 0.1% peracetic acid solution for 2 h with subsequent rinses in phosphate buffered saline and distilled water to disinfect the material and remove any cellular remnants. Two methods may be used to produce a particulate form of UBM. The first method involved lyophilizing the disinfected material and then chopping it into small sheets for immersion in liquid nitrogen. The snap frozen material is then reduced to small pieces with a blender so that the particles were small enough to be placed in a rotary knife mill, such as a Wiley mill. A #60 screen can be used to restrict the collected powder size to less than 250 mm. A Sonic sifter or other classification device can be used to remove larger particles and/or to obtain a particle size distribution within a desired range.

Another method described in Gilbert et al. is similar to the previous method except the disinfected material is first soaked in a 30% (w/v) NaCl solution for 5 min. The material is then snap frozen in liquid nitrogen to precipitate salt crystals, and lyophilized to remove residual water. This material is then comminuted as described in above. By precipitating NaCl within the tissue, it is expected that the embedded salt crystals would cause the material to fracture into more uniformly sized particles. The particles are then suspended in deionized water and centrifuged for 5 min at 1000 rpm three times to remove the NaCl. The suspension is snap frozen and lyophilized again. Finally, the powder is placed in a rotary knife mill to disaggregate the individual particles.

Sonic sifting and laser diffraction can be used to analyze the particle size distribution that resulted from powdering methods, such as the two powdering methods described above. Sonic sifting involves separating the powder by size through a series of graduated screens stacked in a vertical configuration. The powder passes through the screens as a result of sonic pulses along the longitudinal axis of the stack and mechanical agitation in the plane of the screens. The screen sizes, according to one non-limiting embodiment, can be 212, 125, 90, 63, and 38 mm. Finer screens (e.g., electroform meshes) are available, for screening down to 5 µM or less using a Sonic Sifter.

A laser diffraction method may be used to determine the powder size. Each particle diffracts the light, and the diffraction angle is inversely proportional to the size of the particle. The diffraction pattern can be detected using an array of detectors, and the particle size can be calculated based on the angle and intensity observed.

The powdered ECM-derived material can have a range of particulate sizes. By "powdered" or "powder", it is meant that the material has a particulate size distribution sufficiently small so that the material can be inhaled or otherwise delivered to the lungs in sufficient location and quantity to produce the desired and/or stated effect, namely lessening or prevention of pulmonary fibrosis. The powder is typically prepared as a composition in any suitable form for delivery to a subject's airway, for example as a dry powder or combined with a liquid and/or gas in any suitable composition. The optimal sizes and distributions can be determined by routine experimentation, for example, by methods described in the Examples below. Useful particle sizes and distributions include the ranges: less than 250 µM (micrometers, or microns), less than 200 µM, less than 175 µM, less than 150 µM, less than 125 µM, less than 100 µM, less than 75 µM, less than 50 µM, less than 25 µM, less than 10 µM or less than 5 µM, for example less than 75 µM or less than 10 µM. Size distributions can vary greatly, with mean particle sizes ranging from, for example and without limitation, 200 µM, 175 µM, 150 µM, 125 µM, 100 µM, 75 µM, 50 µM, 25 µM, 10 µM or 5 µM, depending on the method of classifying (size fractioning) the powder. The powder can be prepared by any useful method, for instance by physical comminution, crushing, grinding, milling, spray drying, etc. Size fractionation of the particles can be accomplished by any effective method, such as by sieving, sifting, screening, sedimentation, elutriation, etc. See, e.g., Troy, D. B., Editor, Remington: The Science and Practice of Pharmacy, 21$^{st}$ Edition, Lippincott Williams & Wilkins (2005), pp. 702-719 for further description of methods of manufacturing powders.

In one embodiment, the ECM-derived material is solubilized, e.g., by digestion with a protease, such as pepsin, trypsin, collagenase, etc. The solubilized ECM-derived material can then be suspended in any useful pharmaceutically-acceptable solution for use in any airway delivery system, including sprayers, aerosolizers, nebulizers, etc., for example as described herein. Also, the solubilized ECM-derived material may be dried, spray-dried, lyophilized, etc. and comminuted as is necessary to prepare one non-limiting example of a suitable dry powder for either long-term storage or delivery to a subject via a dry powder dosing method, e.g., as are described herein.

The composition can be delivered by any suitable airway delivery device in any fashion, including, without limitation: spraying, aerosolizing, nebulizing, inhaling, or otherwise delivering the composition into a volume of air for dispensation into a subject's airway. Airway delivery devices may contain and deliver only a single dose of a composition such as a drug product, but typically carry multiple (more than one) doses of the composition or drug product, and are referred to as meter dose inhalers. As part of the apparatus described herein, a large number of devices are commercially available for dosing and delivering composition(s) in both dry or liquid (or otherwise) form to a subject's airway. "Airway" is intended to include all parts of a subject's respiratory system extending from the nose and mouth to the lungs, and including, without limitation: nasopharynx, oropharynx, pharynx, laryngopharynx/hypopharynx, larynx, trachea, bronchi, bronchioles, alveolar ducts and alveoli.

For example, dry powder can be dispensed by an airway delivery device that comprises a mechanism for dispensing unit doses, e.g., into a chamber from which the drug product is inhaled by a subject and/or expelled into the subject's airway by any useful mechanism, such as by air flow or pressurized gas. Drug products for certain asthma medications, such as PULMICORT FLEXHALER and ADVAIR DISKUS utilize such delivery devices. Those technologies can readily be applied to the delivery of the powdered ECM-derived materials described herein. The powdered ECM-derived material may be admixed with any pharmaceutically acceptable carrier or carriers or other excipients, including flow enhancers, flavorings, salts, buffers, etc.

The powdered or solubilized material also can be dispensed in any useful spray, aerosol or nebulization airway delivery device. A multitude of such devices are known in the arts. Useful excipients include, without limitation: solvents, such as water and optionally organic solvents, such as an alcohol, buffers, salts, surfactants, flavorings, propellants, such as a fluorocarbon or tetrafluoroethane propellant, rheology modifiers, colorants, preservatives, etc., See, e.g., Troy, D. B., Editor, Remington: The Science and Practice of Pharmacy, 21$^{st}$ Edition, Lippincott Williams & Wilkins (2005), pp. 1000-1017 for exemplary devices and manufacturing methods. The device may deliver the drug via the nose or mouth or intratracheally, by including in addition to the dispenser, an endotracheal tube, or adapter therefor, so that the composition can be delivered into a subject's trachea (see, e.g., U.S. Pat. No. 6,766,801).

Thus provided is an apparatus comprising an airway delivery device comprising a composition comprising a ECM-derived material. Any device useful for delivering a dose of a composition, such as a drug product, to a subject's airway is considered to be an airway delivery device, irrespective of mechanism and physical form of the composition to be delivered or when delivered. For example, any such device described herein is considered to be an 'airway delivery device". The ECM-derived material can be a dry powder or dispersed within a solvent, optionally including a propellant, for aerosolization. The airway delivery system is suitable for delivery of and configured to deliver of one or more unit doses of the composition to a subject's airway, such as a metered dose aerosol delivery system, as are well known in the pharmaceutical arts.

By "prevention" or "preventing", it is not meant absolute prevention of a stated end-result, such as pulmonary fibrosis, but ascertainable reduction of or lessening of fibrosis in a subject, as compared to a subject not treated in the same manner according to the preventative methods described herein. This ability of a therapeutic regimen to "prevent" a stated condition typically is ascertained by controlled studies and is identified by a statistically-significant difference in results that is medically and/or pharmaceutically acceptable (see, e.g., FIG. 2).

Any relevant end-point can be used to determine an amount of ECM-derived material effective to prevent, lessen or treat pulmonary fibrosis in a subject. The amounts effective in a subject in humans or other animals can be tested in animals, for example as described herein. Effective doses can be determined by reference to a therapeutic window between a minimum and maximum dose. The minimum dose is a dosage below which the ECM-derived material is not effective in achieving a desired clinical outcome. The maximum dosage is a dosage above which the drug causes undesirable and/or unacceptable side-effects, including death or other side-effects. The maximum dosage also may be limited by the maximum solubility of the active agent in the drug product composition and the amount of the composition that can be administered at one time. By "effective," it is meant that pulmonary fibrosis is prevented or mitigated (reduced) to a clinically or statistically-relevant degree in a subject or population of subjects acceptable in the medical, pharmaceutical and/or veterinary arts.

The amount of an ECM-derived material useful in preventing or mitigating pulmonary fibrosis in a subject will vary, depending on the material used, and delivery method, among other factors. For example and without limitation, effective unit doses may range from between 10 μg (micrograms) and 1000 mg of the ECM-derived material. In one embodiment, a dry powder of the ECM-derived material is administered by inhalation in a formulation that is suitable for administration by an inhalation route. In another embodiment, a solution comprising, without limitation, from 1 μg/mL to 100 mg/mL, 100 μg/mL to 10 μg/mL or 1 mg/mL to 5 μg/mL, including 4 mg/mL, or increments within any of the stated ranges, of the ECM-derived material is administered to a subject. The material may be administered in a single unit dose or in multiple doses over any suitable and effective time period, for example, from one to ten times daily, every other day, weekly, bi-weekly, monthly, etc. The quantity of ECM-derived material that is administered to a subject depends on the concentration of the active agent in the solution, the size of the subject (a larger subject might better physically tolerate larger amounts of a solution), as well as the maximum tolerable dose and the minimum effective dose, all of which can readily be identified by those of ordinary skill in the art. The composition can be administered prior to, during or after exposure of a subject to a fibrosis-inducing event, such as exposure to chemotherapy or radiotherapy in a cancer patient or exposure of a subject to asbestos or a silicious material.

The ECM-derived material may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts (see, Troy, D B, Editor, Remington: The Science and Practice of Pharmacy, $21^{st}$ Ed., Lippincott Williams & Wilkins (2005) for detailed descriptions of various dosage forms, methods of manufacture of such dosage forms and routes of administration of such dosage forms). Excipients may include compounds or compositions that enhance the solubility of the compound.

Example 1

Regenerative medicine approaches using extracellular matrix (ECM) scaffolds derived from porcine small intestinal submucosa (SIS) and urinary bladder matrix (UBM) have been shown to promote site-specific constructive tissue remodeling in various body systems (Badylak, S. F., Biomaterials, 2007. 28(25): p. 3587-93). The site-specific remodeling response is due in part to rapid degradation with release of bioactive degradation products (Gilbert, T. W., et al., J Bone Joint Surg Am, 2007. 89(3): p. 621-30 and Reing, J. E., et al., Tissue Eng, 2008. In Press) and to modulation of the immune response to an accommodative, non-cytotoxic response (Badylak, S. F. and Gilbert T. W., Semin Immunol, 2008. 20(2): p. 109-16). Based on these findings, the present study tests the hypothesis that UBM-ECM will can promote normal remodeling and prevent fibrosis in the lung using a model of bleomycin-induced pulmonary fibrosis.

Materials and Methods

Ten-week-old C57BL/6 mice were treated by intratracheal instillation with 0.1 mL of a solution comprising 0.05 units of bleomycin or saline vehicle with or without 4 mg/mL of porcine UBM-ECM lyophilized powder (particles <75 μM, produced as previously described (Gilbert, T. W., et al., Biomaterials, 2005. 26(12): p. 1431-5)).

The ECM was isolated from the porcine urinary bladder. The bladders were harvested immediately following euthanasia of market weight pigs (approximately 120 kg). The ECM isolation was performed by removing the tunica muscularis externa and tunica submucosa layers, leaving the basement membrane and tunica propria intact. The UBM was then washed in a 0.1% peracetic acid solution for 2 h with subsequent rinses in phosphate buffered saline and distilled water to disinfect the material and remove any cellular remnants. The disinfected material was lyophilized and then chopped into small sheets for immersion in liquid nitrogen. The snap-frozen material was then reduced to small pieces with a Waring blender so that the particles were small enough to be placed in a rotary knife mill. A Wiley mill fitted with a #60 screen was used to restrict the collected powder size to less than 250 mm.

A Sonic Sifter with a series of mesh was utilized to obtain a fraction having a particle size of <75 Mm. The smallest mesh size was L3S200, for which the opening size is 75 micron. Everything that passed through the last screen was used.

Mice were sacrificed 14 days after exposure and bronchoalveolar lavage fluid (BALF) was collected by instillation and recovery of 0.8 mL of 0.9% saline. Total cell counts, cell differentials, and protein levels in the BALF were obtained. Lungs were inflation fixed with 10% formalin and hematoxylin and eosin staining was performed on lung sections and scored by a pathologist blinded to the sample groups. All comparisons between groups were compared with one-way ANOVA with Tukey's post-test or two-way ANOVA with Bonferroni's post-test using Graphpad Prism 4. A p value of ≤0.05 was considered statistically significant.

Results

To assess inflammation, inflammatory cell accumulation in the BALF post-treatment was determined. Compared to saline-treated and saline with UBM-ECM-treated controls, bleomycin-treated mice with and without UBM-ECM had more inflammatory cells in their BALF. Furthermore, cell differentials revealed that there was a significant increase in macrophages (p<0.001) and modest increases in neutrophils and lymphocytes in both bleomycin and bleomycin with UBM-ECM mice when compared to both saline controls.

Figure 2:
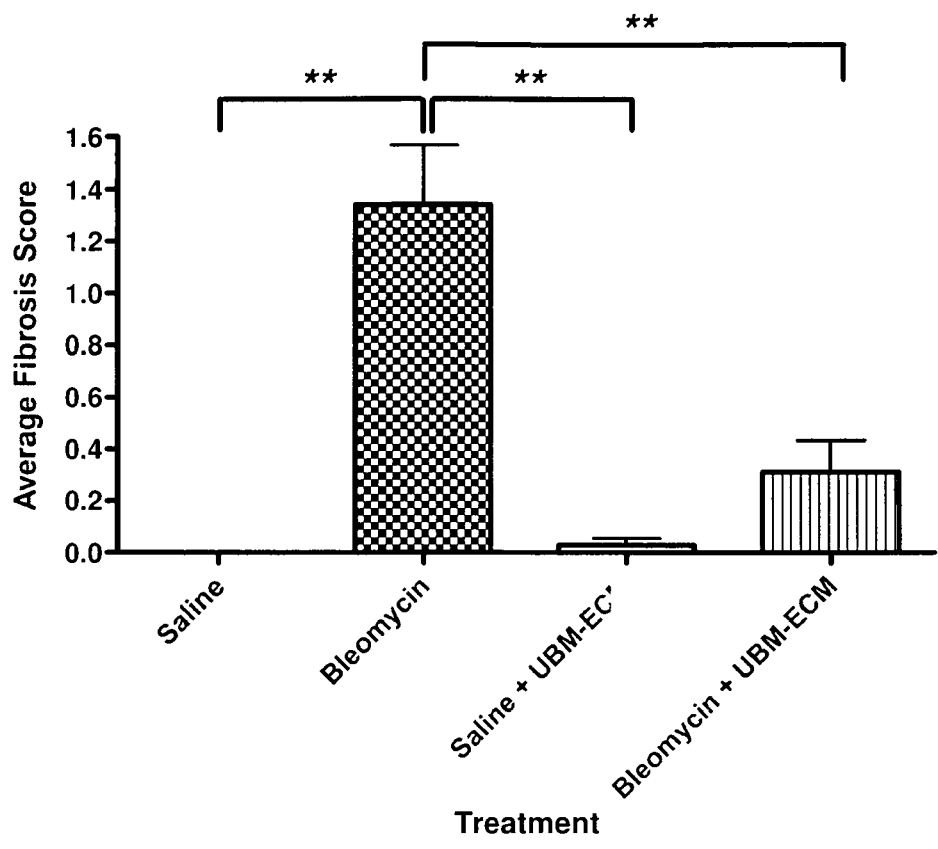
FIG. 2 is a graph showing that UBM-ECM attenuates bleomycin-induced pulmonary fibrosis. Fibrosis was measured in wild type C57BL/6 mice 14 days after exposure. Average histology score was determined by a blinded pathologist and the scoring system was as follows: 0=no fibrosis, 1=0-25% fibrosis, 2=25-50%, 3=50-75%, 4=75-100%. **$p<0.001$.

In contrast to inflammation, the amount of fibrotic injury in the lungs following bleomycin was reduced with UBM-ECM treatment. Mice treated with bleomycin and UBM-ECM trended to have less protein in their BALF than mice treated with bleomycin alone. More impressively, histological examination of the lungs of these mice revealed that mice treated with bleomycin and UBM-ECM had significantly less pulmonary fibrosis than mice treated with only bleomycin (FIG. 2, p<0.001). Finally, treatment with UBM-ECM in saline vehicle revealed that UBM-ECM alone did not cause any histological changes in the lung.

Conclusions

Although there was no change in the amount of inflammation and only a modest decrease in protein in the BALF, UBM-ECM was able to dramatically limit the fibrosis that results from bleomycin injury. Overall, our results strongly suggest that UBM-ECM can minimize bleomycin-induced pulmonary fibrosis.

Example 2

Materials and Methods
Preparation of ECM:

The preparation of UBM and SIS has been previously described (Brown B, Lindberg K, Reing J, Stolz D B, Badylak S F. The basement membrane component of biologic scaffolds derived from extracellular matrix. *Tissue Eng* 2006; 12(3):519-526). Porcine urinary bladders and small intestine were harvested from market weight pigs (approximately 110-130 kg) immediately after sacrifice at an abattoir and transported to the lab on ice. The urothelial layer of the bladders was removed by soaking the material in 1 N saline. The tunica serosa, tunica muscularis externa, tunica submucosa, and most of the muscularis mucosa were mechanically delaminated from the bladder tissue. The remaining basement membrane of the tunica epithelialis mucosa and the subjacent tunica propria were collectively termed UBM. For SIS, the tunica muscularis externa and the majority of the tunica mucosa of the small intestine was removed. The remaining tunica submucosa and basilar portion of the tunica mucosa consists of extracellular matrix and the constituent cells, collectively termed SIS. Both UBM and SIS were decellularized and disinfected by immersion in 0.1% (v/v) peracetic acid (PAA), 4% (v/v) ethanol, and 96% (v/v) deionized water (diH$_2$O) for 2 h. The material was then washed twice for 15 min with PBS (pH=7.4) and twice for 15 min with diH$_2$O (12).

After the ECM material was decellularized and disinfected, the scaffold was lyophilized and chopped into small sheets. The chopped material was then fed through a rotary knife mill. A #60 screen was used to restrict the collected powder size to less than 250 μm. The powder was then sifted through stainless steel mesh on a Sonic Sifter to less than 75 μm. For cell culture and animals studies, the particulate material was terminally sterilized with 2 MRad γ-irradiation (Gilbert T W, Stolz D B, Biancaniello F, Simmons-Byrd A, Badylak S F. Production and characterization of ecm powder: Implications for tissue engineering applications. *Biomaterials* 2005; 26(12):1431-1435). Nonsterile particulate UBM was added to 1 mg/mL pepsin (Sigma) in 0.01 N HCl for a final concentration of 10 mg UBMM/mL suspension. The suspension was mixed on a stir plate at room temperature for approximately 48 hours until no visible pieces of UBM remained. Pepsin buffer control samples were prepared by mixing the pepsin digestion buffer (1 mg/mL pepsin in 0.01 N HCl) at room temperature for 48 hours.

Animals:

All treatments were done intratracheally as previously described (Fattman C L, Chu C T, Kulich S M, Enghild J J, Oury T D. Altered expression of extracellular superoxide dismutase in mouse lung after bleomycin treatment. *Free Radic Biol Med* 2001; 31(10):1198-1207). Ten-week-old C57BL/6 mice were intratracheally instilled with 0.07 units of bleomycin sulfate (Hospira, Inc, Lake Forest, Ill.) with or without 280 μg UBM-ECM powder, SIS-ECM powder, UBM-ECM digest, or pepsin buffer digest control to determine the effect of these ECM compounds on the development of fibrosis. Control mice were treated with 0.9% saline vehicle with and without 280 μg of ECM. Mice were euthanized 14 days after exposure. Bronchoalveolar lavage fluid (BALF) was obtained by the intratracheal instillation and recovery of 0.8 ml of 0.9% saline as previously described (Fattman C L, et al., *Free Radic Biol Med* 2001; 31(10):1198-1207). Lungs were inflation fixed with 10% buffered formalin and paraffin embedded for histological analysis.

Bronchoalveolar Lavage Fluid:

Total protein was determined by use of the Coomassie Plus Protein Assay Reagent (Pierce, Rockford, Ill.). Total white blood cell counts were obtained with a Beckman Z1 Coulter particle counter (Beckman Coulter, Fullerton, Calif.). To obtain a differential count, bronchoalveolar lavage (BAL) fluid samples were adhered to glass slides with a cytospin, stained with DiffQuik, and the numbers of macrophages, neutrophils, lymphocytes, and eosinophils were counted under a microscope. A total of 400 cells were counted per slide. The remaining BAL fluid was spun down at 200×g and supernatants were stored at −70° C. until use for protein and cytokine analyses.

Histology and Fibrosis Scoring:

Standard hematoxylin and eosin staining was performed on 5-μm-thick lung sections as previously described (Fattman C L, et al., *Free Radic Biol Med* 2001; 31(10):1198-1207). Hematoxylin and eosin-stained sections were scored as previously described (Englert J M, et al. A role for the receptor for advanced glycation end products in idiopathic pulmonary fibrosis. *Am J Pathol* 2008; 172(3):583-591 and Fattman C L, et al. Increased sensitivity to asbestos-induced lung injury in mice lacking extracellular superoxide dismutase. *Free Radic Biol Med* 2006; 40(4):601-607) by a pathologist (T.D.O.) who was blinded to sample groups. Individual fields were examined with a light microscope at ×200 magnification. Briefly, every field in the entire lung was scored, starting peripherally. To be counted, each field had to contain alveolar tissue in >50% of the field. Scoring in each field was based on the percentage of alveolar tissue with interstitial fibrosis according to the following scale: 0=no fibrosis, 1=up to 25%, 2=25-50%, 3=50-75%, 4=75-100%. The pathological index score was then reported as a ratio of the sum of all of the scores divided by the total number of fields counted for each sample. Group scores were averaged for statistical analyses.

Toxicity Assay:

A549 human epithelial cells (ATCC) were cultured in F12K media supplemented with 10% fetal bovine serum (FBS). A549 cells were plated on 96 well plates (5,000 cells/well). Cells were serum starved for 4 hrs prior to treatment with either 0.02 units of bleomycin, or bleomycin with various amount of ECM as indicated in serum-free media. 24 hr following treatment, cell viability was measured using CellTiter 96 AQ Non-radioactive Assay according to manufacturer's instructions (Promega, Madison, Wis.).

Chemotaxis Assay:

Responses of epithelial cells to UBM degradation products were quantitatively evaluated utilizing the Neuro Probe 48-well microchemotaxis chamber (Neuro Probe, Gaithersburg, Md.). A549 cells were serum-starved for 14-17 h prior to experimentation. Based upon pilot studies to determine the appropriate filter pore size, 5 μm polycarbonate chemotaxis filters (Neuro Probe, PFB5) were coated equally on both sides (by immersion) with 0.05 mg/mL rat tail collagen I (BD Biosciences, San Jose, Calif.) and allowed to dry prior to chamber assembly. 27.5 μL of F12K media (Cellgro, 10-025-CV), F12K media supplemented with 10% FBS, 0.5 mg/mL UBM digest, 0.1 mg/mL UBM digest, 0.5 mg/mL Pepsin digest, and 0.1 mg/mL Pepsin digest was added to the bottom chamber wells. The filter was placed over the bottom chamber, and the apparatus was assembled according to the manufacturer's instructions. Approximately 30,000 cells were then added to each upper chamber well of the apparatus, and the chamber was incubated for 4 h at 37° C. in a humidified atmosphere in 95% air:5% $CO_2$. Cells remaining on the topside of the membrane (i.e., nonmigrated cells) were removed, and then cells on the bottom side of the membrane (i.e., migrated cells) were stained with Diff Quik (Dade AG, Liederbach, Germany). The filter was then mounted with Vectashield containing DAPI (Vector Laboratories, H-1200) and fluorescent images of each conditioned well were captured at 10× magnification using a Nuance multispectral imaging system and Nikon microscope. Each experimental condition was tested in quadruplicate in three independent experiments. The average number of migrated cells in each experiment was normalized to the positive control (10% FBS) by calculating the average percentage of migrated cells as a percentage of the positive control for each condition.

Wound Healing Assay:

A549 cells cultured in F12K media (Cellgro 10-025-CV) supplemented with 10% FBS were seeded and grown to confluence in a 6-well plate. Cells were serum starved in non-supplemented F12K media overnight prior to initiation of the experiment. Straight wounds were created as previously described (Liang C C, et al. In vitro scratch assay: A convenient and inexpensive method for analysis of cell migration in vitro. *Nat Protoc* 2007; 2(2):329-333) by scratching vertically with a p-200 micropipette tip. The wounds were then washed and treated with the following experimental conditions: 0.075 U/mL Bleomycin; 0.075 U/mL Bleomycin+0.5 mg/mL UBM powder; 0.075 U/mL Bleomycin+0.5 mg/mL UBM digest; 0.075 U/mL Bleomycin+0.5 mg/mL Pepsin digest; and 0.5 mg/mL UBM digest. Images were captured at 0 and 24 hours after addition of treatments. Using ImageJ, average wound widths in pixels were obtained for each well at each time point.

Statistical Analyses.

The significance of all quantitative data was assessed using either a Students t-test or one-way ANOVA with Tukey's post-test (for comparison of 3 or more groups). Data was analyzed using the computer program Prism (GraphPad Software, San Diego, Calif.). A p-value of less than or equal to 0.05 was considered statistically significant.

Results

UBM-ECM Prevents Bleomycin-Induced Pulmonary Fibrosis

Figure 3:
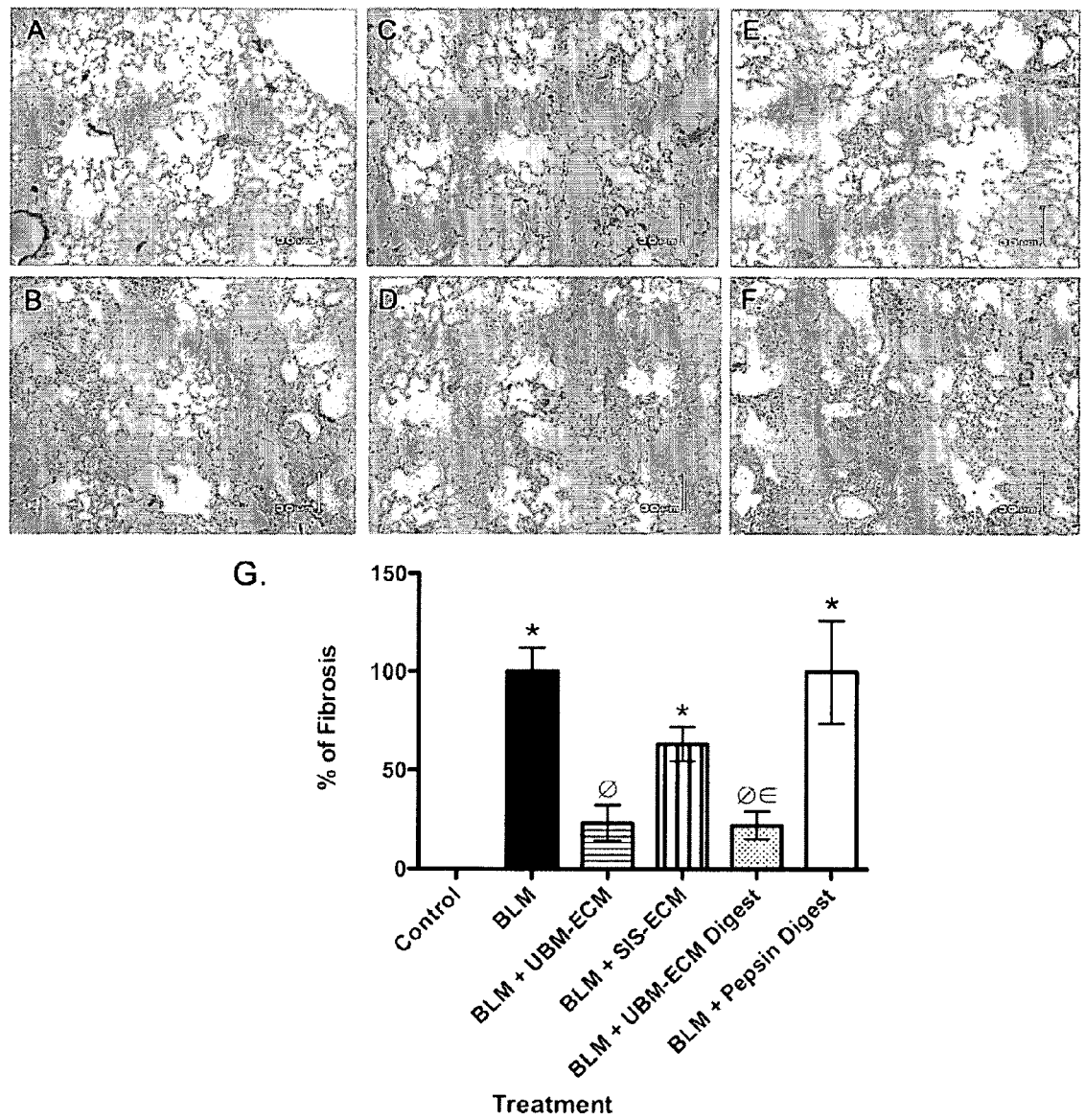
FIG. 3. UBM-ECM prevents bleomycin-induced fibrosis. Wild-type mice were euthanized 14 days after intratracheal administration of bleomycin. Histological analyses revealed that UBM-ECM limited pulmonary fibrosis: A. Vehicle B. Bleomycin (BLM) C. BLM & UBM-ECM D. BLM & SIS-ECM E. BLM & UBM-ECM Digest F. BLM & Pepsin Digest E. Average histology score was determined by a pathologist (T.D.O.) blinded to treatment groups. The scoring system was as follows: 0=no fibrosis, 1=0-25% fibrosis, 2=25-50% fibrosis, 3=50-75% fibrosis, 4=75-100% fibrosis. All scores were reported as the percentage of fibrosis when compared to bleomycin treatment alone (100% fibrosis) except UBM-ECM digest, which was normalized to its control pepsin digest. Vehicle image is representative of the following treatments: saline, UBM-ECM, SIS-ECM, UBM-ECM digest, or pepsin digest. Results shown are representative of n=4-7/treatment group. *$p<0.05$ when compared to control, †$p<0.05$ when compared to bleomycin, ¥$p<0.05$ when compared to bleomycin+pepsin digest, one-way ANOVA.

Histologic analyses of the lungs showed a significant reduction in fibrosis in the lungs of bleomycin-treated mice that received UBM-ECM (FIG. 3C) or UBM-ECM digest (FIG. 3E) when compared to the mice that received bleomycin alone (FIG. 3B) or bleomycin and pepsin digest control (FIG. 3D) respectively. In contrast, bleomycin treated mice that received SIS-ECM (FIG. 3F) showed fibrosis that was not significantly different from bleomycin alone. These differences in fibrosis were quantified by histologic scoring (FIG. 3G). Administration of ECM alone did not cause any adverse effects and the lungs were pathologically identical to the saline controls (data not shown).

Figure 4:
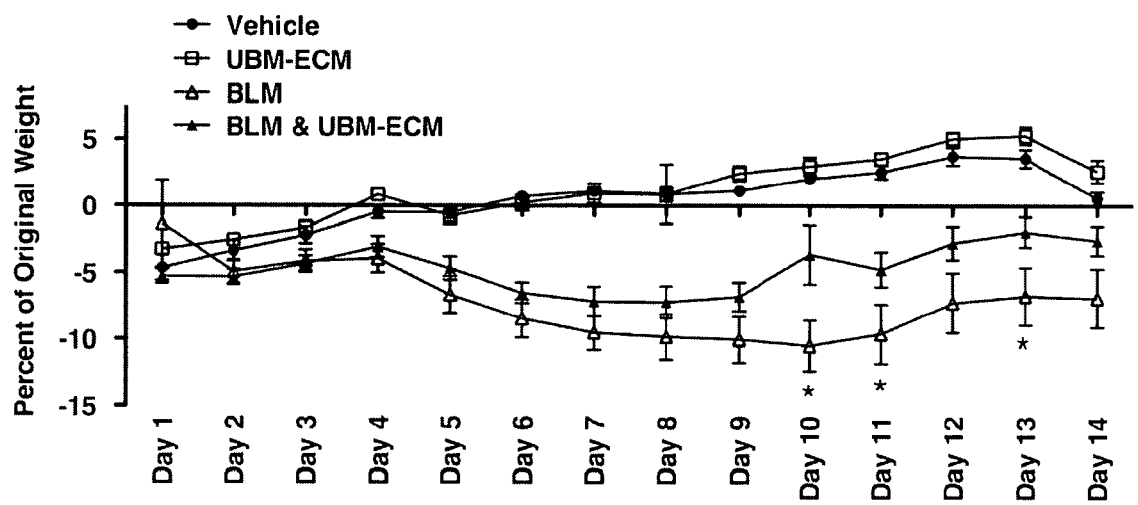
FIG. 4. Treatment with ECM does not prevent bleomycin-induced leukocyte accumulation. All bleomycin-treated mice have increased total cells in their BALF (A-C) and specifically significantly more macrophages and modest increases in neutrophils and lymphocytes (D-F) regardless of ECM treatment. Results shown are representative of three independent experiments (n=4-7/group/experiment). Vehicle=saline or TiO2 controls. *$p<0.05$ compared to vehicle control, †$p<0.05$ compared to UBM-ECM control, ¥$p<0.01$ compared to vehicle and UBM-ECM control, §$p<0.05$ compared to BLM or BLM+Pepsin Digest FIG. 5. ECM treatment does not affect bleomycin toxicity. A549 cells (5,000 cells/well) were serum starved for 4 hrs and then incubated with serum-free F12K media, 0.02 units of bleomycin (BLM), and BLM with indicated amounts of UBM-ECM (A), SIS-ECM (B), or UBM-ECM digest (C) for 24 hours. Cell viability was measured using Promega CellTiter 96® AQueous Non-Radioactive Cell Proliferation Assay according to manufacturer's instructions ($OD_{490}$) and reported as the percentage of viable cells when compared to media control. *$p<0.05$ when compared to media control.

There was an increase in the number of leukocytes within the BAL fluid following bleomycin exposure regardless of ECM treatment (FIG. 4A-C). The BAL fluid differentials showed a significant increase in macrophages and modest increases in neutrophils and lymphocytes in the BALF of mice treated with bleomycin and bleomycin with various ECM treatments when compared to controls (FIG. 4D-F).

UBM-ECM Does Not Affect Bleomycin Toxicity

Figure 5:
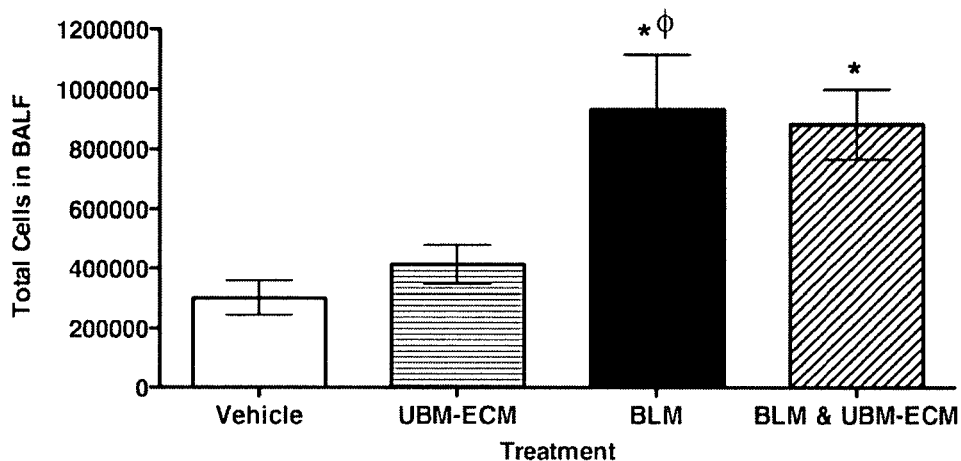
Figure 5:
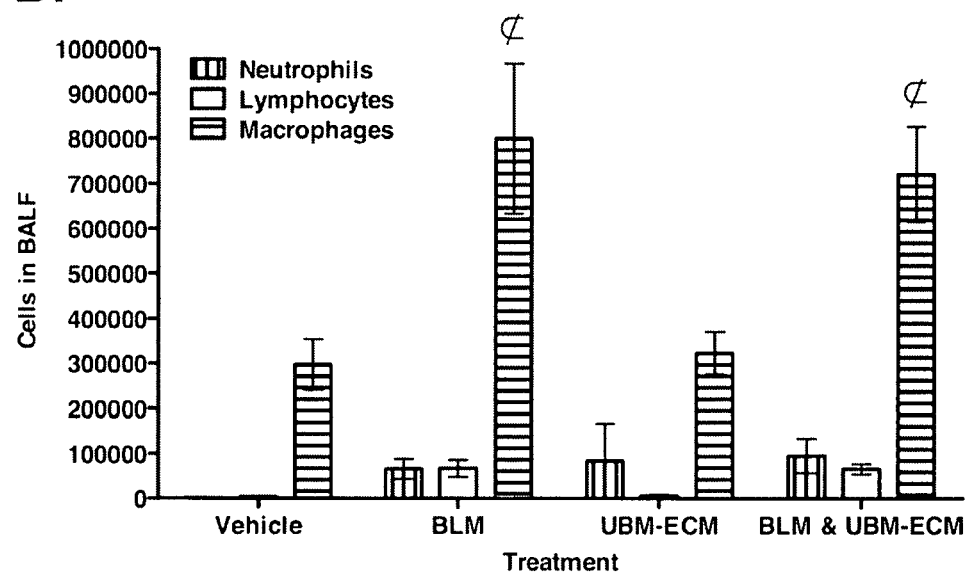

A549 cells were treated with bleomycin and different doses of UBM-ECM, SIS-ECM, or ECM digest to verify that the presence of the ECM scaffold material does not alter the toxicity of the bleomycin. These results showed that reduction in cell viability caused by bleomycin was not significantly altered due to bleomycin treatment simultaneous with UBM-ECM (FIG. 5A), SIS-ECM (FIG. 5B), or UBM-ECM Digest (FIG. 5C).

UBM-ECM Promotes Migration of Epithelial Cells

Figure 6:
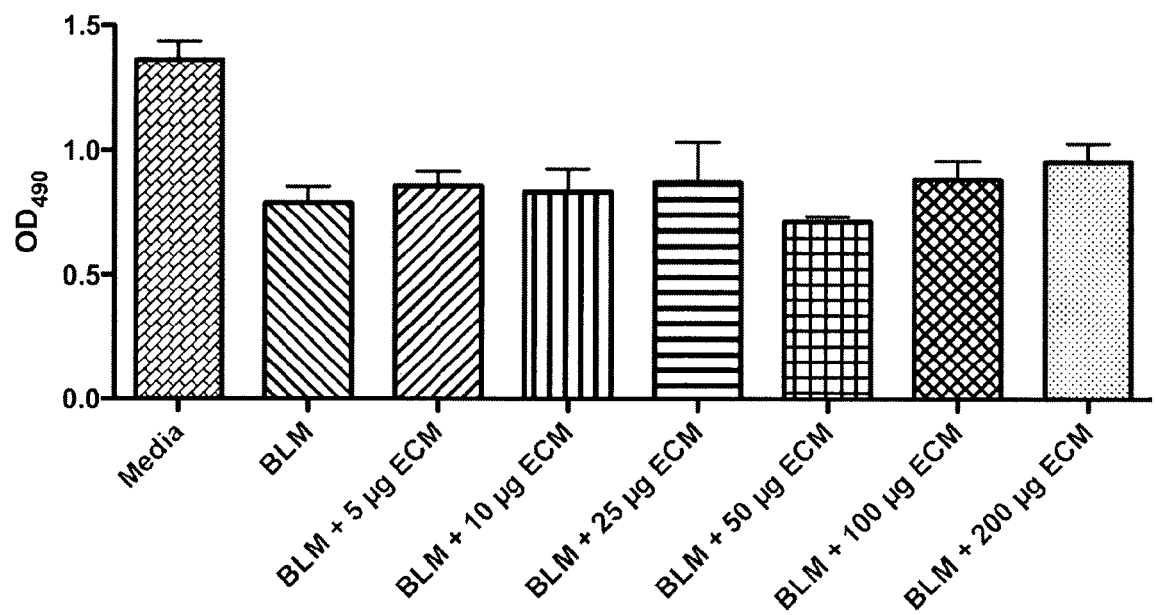
FIG. 6. ECM promotes chemotaxis of epithelial cells. Chemotaxis of serum-starved A549 cells (30,000 cells/well) was quantitatively evaluated utilizing the Neuro Probe 48-well microchemotaxis chamber. Chemotaxis toward F12K media with 10% FBS (positive control), serum-free F12K media, and 100 µg/mL and 500 µg/mL UBM-ECM digest or control pepsin digest was measured in quadruplicate in three independent experiments. The average percentage of migrated cells for each condition was normalized to the average percentage of cells that migrated toward the media with 10% FBS (positive control) in each experiment. *$p<0.05$ when compared to 10% FBS FIG. 7. UBM-ECM stimulates re-epithelialization. A549 cell monolayers were serum-starved for 24 hrs, wounded, and exposed to UBM-ECM digest, bleomycin (BLM), BLM with UBM-ECM powder or digest, or BLM with pepsin digest control. Results were reported as the percentage of change in wound width over 24 hrs. *$p<0.05$ when compared to UBM-ECM digest control treatment

Migration of serum-starved A549 cells towards the UBM-ECM digest approached the migration promoted by the positive control, 10% FBS (FIG. 6). The UBM digest at 500 μg/ml concentration showed 94%±35% of the cell migration observed for the positive control, while 100 μg/ml concentration showed 73%±20% of the cell migration observed for the positive control. The relative cell migration towards the pepsin digest controls were 23%±17% and 19%±18% for 500 μg/ml and 100 μg/ml concentration respectively. The migration toward both concentrations of pepsin digest was similar to the F12K media alone (13%±11%). At both concentrations, the UBM-ECM digest showed significantly improved migration compared to the pepsin digest control (FIG. 6).

Figure 7:
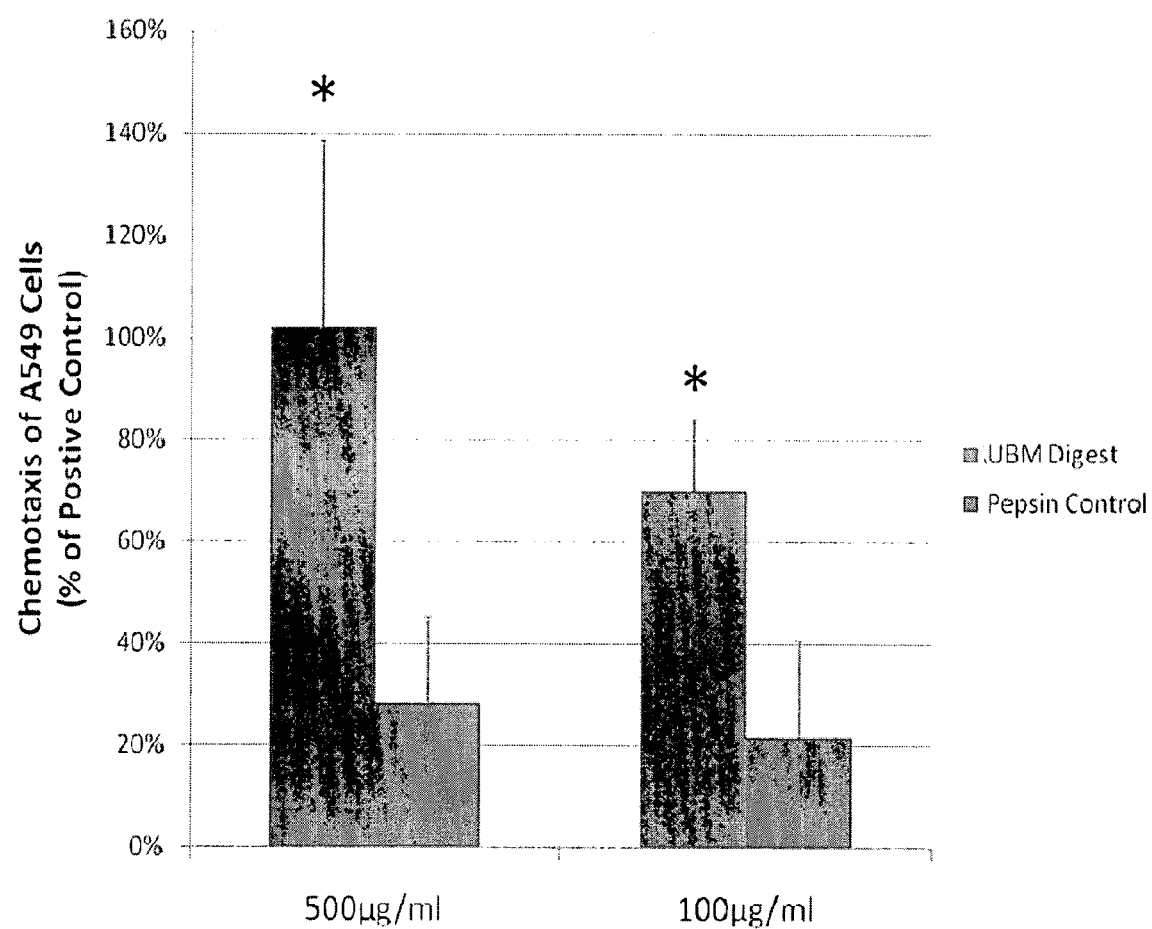

Using a wound healing assay, serum-starved A549 cells were treated with UBM-ECM or UBM-ECM digest in the presence of bleomycin to evaluate the ability of ECM to improve wound repair. UBM-ECM digest treatment promoted wound closure in the presence of bleomycin while pepsin digest control did not affect wound width (FIG. 7). UBM-ECM treatment showed a trend toward improved wound closure, but did not significantly reduce wound width in the presence of bleomycin.

UBM-ECM scaffold material prevented bleomycin-induced pulmonary fibrosis when delivered simultaneously with the bleomycin regardless of the form (particulate or digested) of the material. UBM-ECM treatment significantly reduced the histologic presentation of fibrosis, such that there was no significant difference between the histologic appearance of the lungs in animals treated with bleomycin and UBM-ECM as compared to those treated with the saline alone. In contrast, simultaneous treatment of bleomycin exposed animals with SIS-ECM showed a significant increase in fibrosis as compared to saline alone. The SIS-ECM treated group tended to have less fibrosis than bleomycin alone, but was not significantly different. It is clear that the attenuation of fibrosis in response to UBM-ECM was not due to neutralization of the bleomycin as cell culture studies showed that UBM-ECM did not prevent cell death. Furthermore, animals treated with bleomycin and ECM products had the same increase in the number of inflammatory cells and similar cellular composition in the BAL fluid as animals treated with bleomycin alone. These results suggest that UBM-ECM limited bleomycin-induced fibrogenesis and did not do so by interfering with the effects of bleomycin.

Epithelial cell damage and cell death causes gaps in the epithelial basement membrane allowing for fibroblast migration, which then promote fibrosis. The different responses observed in response to UBM-ECM and SIS-ECM suggests a role for the basement membrane in the reparative process. UBM-ECM is known to possess an intact basement membrane, while SIS-ECM lacks the basement membrane due to the specific tissue layers from which each is isolated (Brown B, Lindberg K, Reing J, Stolz D B, Badylak S F. The basement membrane component of biologic scaffolds derived from extracellular matrix. *Tissue Eng* 2006; 12(3):519-526). The presence of a basement membrane structure has been shown to promote healing in various organs, including the lungs, by providing guidance for re-epithelialization and separating the epithelium from the interstitial connective tissue (Vracko R. Basal lamina scaffold-anatomy and significance for maintenance of orderly tissue structure. *Am J Pathol* 1974; 77(2): 314-346). This is consistent with the findings of previous studies in which UBM-ECM promoted the formation of a pseudostratified, columnar, ciliated epithelium when used for patch tracheoplasty in a dog model (Gilbert T W, Gilbert S, Madden M, Reynolds S D, Badylak S F. Morphologic assessment of extracellular matrix scaffolds for patch tracheoplasty in a canine model. *Ann Thorac Surg* 2008; 86(3):967-973; discussion 973-974). Furthermore, chemotaxis experiments in the present study showed that the digested form of UBM-ECM promoted migration of airway epithelial cells. These findings suggest that the presence of UBM-ECM promotes re-epithelialization at the site of airway epithelial injury caused by bleomycin.

Furthermore, the findings suggest that degradation of the ECM is an important component of the host response. Previous studies have shown that ECM degradation products recruit progenitor cells to the site of remodeling (Beattie A J, et al. Chemoattraction of progenitor cells by remodeling extracellular matrix scaffolds. *Tissue Eng* 2008; doi: 10.1089/ten.tea.2008.0162; Brennan E P, et al. *J Tissue Eng Regen Med* 2008; 2(8):491-498; and Reing J E, et al. Degradation products of extracellular matrix affect cell migration and proliferation. *Tissue Eng Part A* 2009; 15(3):605-614), promote angiogenesis (Li F, et al. Low-molecular-weight peptides derived from extracellular matrix as chemoattractants for primary endothelial cells. *Endothelium* 2004; 11(3-4): 199-206), and provide bacteriostasis (Brennan E P, et al. Antibacterial activity within degradation products of biological scaffolds composed of extracellular matrix. *Tissue Eng* 2006; 12(10):2949-2955). In vivo studies have shown that ECM scaffolds degrade within 3 months after implantation to repair load bearing tissues (Gilbert T W, et al. Degradation and remodeling of small intestinal submucosa in canine achilles tendon repair. *J Bone Joint Surg Am* 2007; 89(3):621-630 and Record R D, et al. In vivo degradation of $^{14}$c-labeled small intestinal submucosa (sis) when used for urinary bladder repair. *Biomaterials* 2001; 22(19):2653-2659). The kinetics of ECM degradation after instillation into an injured lung is unknown and would require additional study.

Based on previous studies, it is known that oxidative fragmentation of ECM components such as heparin sulfate and collagen influence the development of fibrosis (Gao F, et al. Extracellular superoxide dismutase inhibits inflammation by preventing oxidative fragmentation of hyaluronan. *J Biol Chem* 2008; 283(10):6058-6066; Kliment C R, et al. Oxidative stress alters syndecan-1 distribution in lungs with pulmonary fibrosis. *J Biol Chem* 2009; 284(6):3537-3545; and Kliment C R, et al. Extracellular superoxide dismutase protects against matrix degradation of heparan sulfate in the lung. *Antioxid Redox Signal* 2008; 10(2):261-268). However, the present study showed that intact particulate UBM-ECM and enzymatically digested UBM-ECM prevented fibrosis. It is known that ECM scaffold material is a mixture of ECM proteins and other substances, such as growth factors (Badylak S F, et al. Extracellular matrix as a biological scaffold material: Structure and function. *Acta Biomater* 2009; 5(1): 1-13). It is likely that this complex composition of ECM promotes healing that outweighs the detrimental effects of the proteoglycans and glycosoaminoglycans degradation products in these ECM materials.

In conclusion, this study shows that basement membrane containing ECM protected against pulmonary fibrosis using a bleomycin model. These findings also strongly suggest that one mechanism in which this ECM material prevents fibrosis is by promoting epithelial cell chemotaxis and re-epithelialization. These results support the conclusion that ECM will have therapeutic benefit if administered after injury has begun. These findings also suggest that ECM would be useful in attenuation of the response to chronic environmental irritants, such as asbestos and silica, and in different forms of pulmonary fibrosis, and in modulation of immune response.

Example 3

Figure 8:
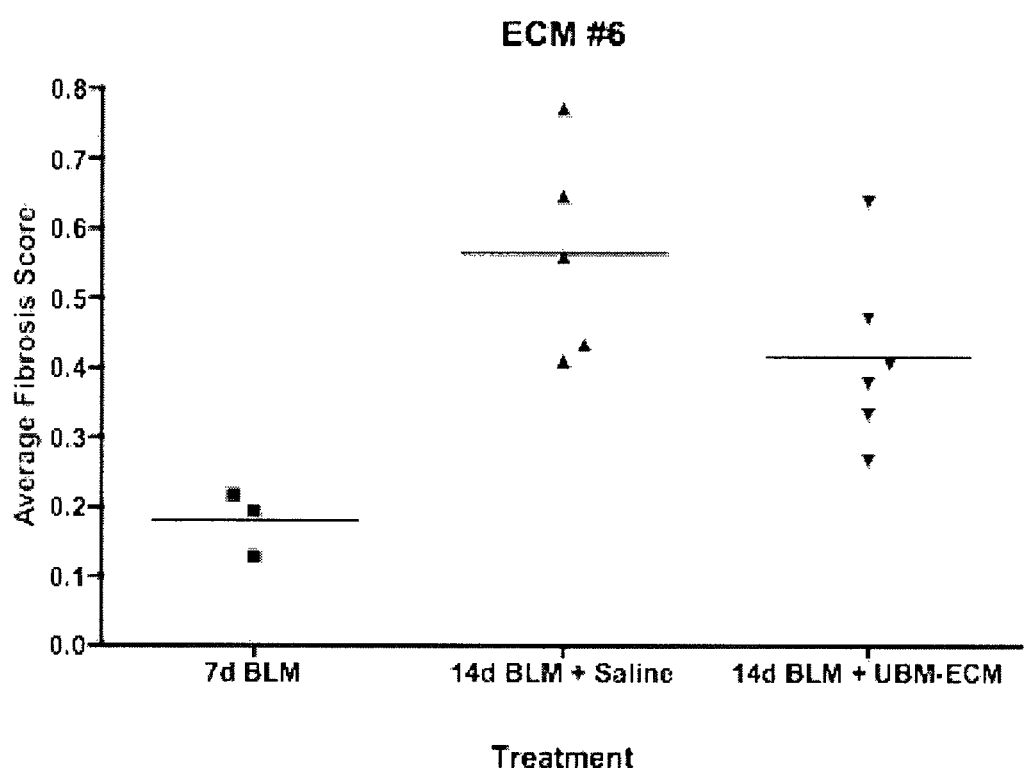
FIG. 8 is a graph showing the effects of ECM on development of pulmonary fibrosis from treatment with a chemotherapeutic agent, as described in Example 3

Chemotherapy and radiotherapy patients often develop pulmonary fibrosis. Drugs such as bleomycin, cyclophosphamide, busulfan, chlorambucil, oxaliplatin, 5-fluorouracil, and nitrosourea drugs are known to cause pulmonary fibrosis. Delivery of the ECM powder could also be used to prevent pulmonary fibrosis in patients being treated with radiation therapy. Therefore, in an extension of the work described above, C57BL/6 mice were intratracheally instilled with 0.07 units of bleomycin sulfate (Hospira, Inc, Lake Forest, Ill.) or 0.9% saline as a control (total of 70 μL/mouse). Seven days after administration of bleomycin sulfate or saline, mice were intratracheally treated with 280 μg ECM-derived material described above in Example 1 or 0.9% saline control (total of 70 μL/mouse) to see if ECM-derived material could prevent further development of fibrosis as shown in FIG. 8. This further illustrates that ECM-derived material is potentially useful as a treatment or pre-treatment for patients undergoing chemotherapy and radiotherapy.

Having described this invention, it will be understood to those of ordinary skill in the art that the same can be performed within a wide and equivalent range of conditions, formulations and other parameters without affecting the scope of the invention or any embodiment thereof.

We claim:

1. A method of reducing interstitial lung disease in a subject in need thereof, comprising:
administering via the subject's airway a composition comprising a devitalized, decellularized layer of extracellular matrix material that is delaminated from one or more layers of a devitalized epithelial tissue in an amount effective to reduce interstitial lung disease in the subject.

2. The method of claim 1, in which the airway delivery system is a metered dose inhaler.

3. The method of claim 1, in which the airway delivery system is a metered-dose inhaler and the composition comprises a propellant.

4. The method of claim 1, in which the composition is a dry powder.

5. The method of claim 4, in which the powdered composition has a maximum particle size of 250 μM.

6. The method of claim 4, in which the powdered composition has a maximum particle size of 75 μM.

7. The method of claim 1, in which the composition is a liquid.

8. The method of claim 1, wherein the interstitial lung disease is associated with silicosis; asbestosis; berylliosis; hypersensitivity pneumonitis; drug induced interstitial lung disease, connective tissue disease, systemic sclerosis, dermatomyositis, systemic lupus erythematosus, rheumatoid arthritis; infection, atypical pneumonia, pneumocystis pneumonia (PCP), tuberculosis; idiopathic interstitial lung disease, sarcoidosis, idiopathic pulmonary fibrosis, Hamman-Rich syndrome, a malignancy, or lymphangitic carcinomatosis.

9. The method of claim 1, wherein between 10 µg and 1000 mg of the composition is delivered to the subject.

10. The method of claim 1, in which the composition comprises epithelial basement membrane.

11. The method of claim 1, in which the composition comprises tunica propria.

12. The method of claim 11, in which the composition further comprises submucosa.

13. The method of claim 1, in which the composition is administered to a subject prior to or after chemotherapy or radiotherapy.

14. The method of claim 1, in which the composition is administered to a subject exposed to a chemical agent.

15. The method of claim 1, in which the composition is solubilized.

16. The method of claim 1, wherein the administering of the composition to the subject's airway is prior to, during or after exposure to a fibrosis-inducing event.

17. The method of claim 1, wherein the administering of the composition to the subject's airway is prior to, during or after exposure to chemotherapy.

* * * * *